(12) United States Patent
Madsen et al.

(10) Patent No.: US 11,896,789 B2
(45) Date of Patent: Feb. 13, 2024

(54) SHUNT FLUSHER

(71) Applicant: Children's Medical Center Corporation, Boston, MA (US)

(72) Inventors: Joseph Madsen, Boston, MA (US); Tomer Anor, Brookline, MA (US)

(73) Assignee: Children's Medical Center Corporation, Boston, MA (US)

(*) Notice: Subject to any disclaimer, the term of this patent is extended or adjusted under 35 U.S.C. 154(b) by 1065 days.

(21) Appl. No.: 16/654,921

(22) Filed: Oct. 16, 2019

(65) Prior Publication Data

US 2020/0147356 A1 May 14, 2020

Related U.S. Application Data

(63) Continuation of application No. 14/773,625, filed as application No. PCT/US2014/020082 on Mar. 4, 2014, now Pat. No. 10,471,239.

(Continued)

(51) Int. Cl.
*A61M 27/00* (2006.01)
*A61M 5/142* (2006.01)
(Continued)

(52) U.S. Cl.
CPC ...... *A61M 27/006* (2013.01); *A61M 5/14276* (2013.01); *A61M 2025/0019* (2013.01);
(Continued)

(58) Field of Classification Search
CPC ........ A61M 2025/0019; A61M 27/006; A61M 2202/0464
See application file for complete search history.

(56) References Cited

U.S. PATENT DOCUMENTS 3,111,125 A 11/1963 Schulte
3,452,757 A 7/1969 Ames
(Continued)

FOREIGN PATENT DOCUMENTS

EP 2 436 419 A1 4/2012
JP H03-029665 A 2/1991
(Continued)

OTHER PUBLICATIONS

Extended European Search Report for Application No. EP14770962.0 dated Aug. 18, 2016.
(Continued)

*Primary Examiner* — Leslie R Deak
(74) *Attorney, Agent, or Firm* — Wolf, Greenfield & Sacks, P.C.

(57) ABSTRACT

A device and system for flushing a shunt catheter utilizes the available cerebrospinal fluid (CSF) to flush a blocked catheter. The CSF is pressurized to a predetermined amount and then allowed to suddenly, rapidly and forcefully purge any occlusions. The rapid release of CSF produces flow jets from the catheter pores into the ventricle. This impulse, or "cough", will push and divert choroid plexus and/or other blockages away from the pores. The device and system may then be allowed to refill at a slow rate, thus reducing the possibility of rapid suction of fluid back into the system and the attendant possibility of drawing the choroid plexus back into the pores. The catheter at the proximal end may also include back-up pores that can be opened to restart flow from the ventricle should the primary pores remain blocked after a flushing attempt.

14 Claims, 11 Drawing Sheets

Related U.S. Application Data (60) Provisional application No. 61/787,922, filed on Mar. 15, 2013.

(51) Int. Cl.
*A61M 39/22* (2006.01)
*A61M 25/00* (2006.01)

(52) U.S. Cl.
CPC ............... *A61M 2039/224* (2013.01); *A61M 2202/0464* (2013.01); *A61M 2210/0693* (2013.01)

(56) References Cited

U.S. PATENT DOCUMENTS

| | | |
|---|---|---|
| 3,492,996 A | 2/1970 | Fountain |
| 3,595,240 A | 7/1971 | Mishler |
| 3,827,439 A | 8/1974 | Schulte et al. |
| 4,464,168 A | 8/1984 | Redmond et al. |
| 4,741,730 A | 5/1988 | Dormandy et al. |
| 4,850,955 A | 7/1989 | Newkirk |
| 4,861,331 A | 8/1989 | East et al. |
| 4,867,741 A | 9/1989 | Portnoy |
| 5,154,693 A | 10/1992 | East et al. |
| 5,304,114 A | 4/1994 | Cosman et al. |
| 5,387,188 A | 2/1995 | Watson |
| 6,193,682 B1 | 2/2001 | Ahmed |
| 7,235,060 B2 | 6/2007 | Kraus |
| 10,471,239 B2 | 11/2019 | Madsen et al. |
| 2002/0128588 A1 | 9/2002 | Borgesen |
| 2004/0260249 A1 | 12/2004 | Kulessa |
| 2010/0121250 A1 | 5/2010 | Pizzi |
| 2012/0123323 A1 | 5/2012 | Kagan et al. |
| 2012/0232461 A1 | 9/2012 | Seaver et al. |
| 2012/0232462 A1 | 9/2012 | Miethke |
| 2012/0302938 A1 | 11/2012 | Browd et al. |
| 2016/0038724 A1 | 2/2016 | Madsen et al. |

FOREIGN PATENT DOCUMENTS

| | | | |
|---|---|---|---|
| WO | WO 83/01387 A1 | 4/1983 | |
| WO | WO 91/17779 A1 | 11/1991 | |
| WO | WO 2007/092875 A2 | 8/2007 | |
| WO | WO 2011/146757 A2 | 11/2011 | |
| WO | WO-2012033420 A2 * | 3/2012 | .......... A61M 27/006 |
| WO | WO 2014/116640 A1 | 7/2014 | |
| WO | WO 2014/149648 A1 | 9/2014 | |

OTHER PUBLICATIONS

Extended European Search Report for European Application No. 18203362.1 dated Nov. 22, 2018.

International Preliminary Report on Patentability for Application No. PCT/US2014/020082 dated Sep. 24, 2015.

International Search Report and Written Opinion for PCT/US2014/020082 dated Jun. 6, 2014.

* cited by examiner

SHUNT FLUSHER

RELATED APPLICATIONS

This application claims the benefit under 35 U.S.C. § 120 and is a continuation of U.S. application Ser. No. 14/773,625, entitled "SHUNT FLUSHER" and filed Sep. 8, 2015, which is a national stage filing under 35 U.S.C. 371 of International Application No. PCT/US2014/020082, entitled "SHUNT FLUSHER" and filed Mar. 4, 2014. International Application No. PCT/US2014/020082 claims priority under 35 U.S.C § 119(e) to U.S. Provisional Application Ser. No. 61/787,922, entitled "SHUNT FLUSHER" and filed Mar. 15, 2013. The entirety of each of the documents listed above is incorporated herein by reference.

BACKGROUND

1. Field

Aspects herein relate to devices and systems cooperating with shunt systems to flush occlusions in or near shunt catheters and in particular to devices and systems cooperating with shunts used to treat hydrocephalus.

2. Discussion of Related Art

Hydrocephalus is a condition in which cerebrospinal fluid (CSF) is unable to drain through natural mechanisms and instead accumulates in the ventricles of the brain. Conventional treatment of hydrocephalus includes the use of a shunt catheter or other drain tube having a proximal end inserted into the ventricle(s) and the opposite, distal end of the tube emptying into the abdominal cavity. The proximal end of the catheter includes one or more pores through which the CSF can enter and flow to the abdominal cavity. A one-way check valve is often included in the line, typically closer to the proximal end of the shunt. The valve acts to maintain the proper pressure in the ventricles, yet allow drainage of CSF to the abdominal cavity.

Shunt obstruction can occur at any time after insertion, and all points along the shunt course are suspect when assessing for shunt malfunction. Shunt obstruction usually presents with clinical evidence of raised intracranial pressure. The presentation is age-dependent, with infants usually having nausea, vomiting, irritability, and a bulging fontanel. Older children and adults usually present with headache, nausea, vomiting, cranial nerve palsies, and ataxia among other neurologic findings.

The most common location for obstruction is the ventricular catheter tip, which can be blocked by ingrowth of choroid plexus. Currently, this kind of obstruction of a shunt is only managed by surgical revision. Revision typically begins by opening the cranial incision to assess the outflow from the ventricular catheter. When the ventricular catheter is obstructed, cerebrospinal fluid flow is diminished or absent completely. Obstruction isolated to the ventricular catheter with adequate distal flow is treated by removal and replacement with a new catheter with similar specifications for length and diameter. Commonly, the ventricular catheter is obstructed by ingrowth of choroid plexus into the lumen of the ventricular catheter tip. Removal in this circumstance is complicated by the risk of bleeding caused by avulsion of choroid plexus if the catheter is forcefully removed.

Some of the existing shunt systems allow back flushing, a process that uses the CSF present in the shunt system to remove the obstructing matter.

SUMMARY

The inventors have found that the use of conventional back flushing arrangements have limitations and can be ineffective altogether due to the small amount of flushing liquid available in existing shunt systems. Moreover, using these built-in mechanisms for flushing may make the situation even worse—a more severe clogging is expected due to rapid suction of CSF back into the catheter and/or chamber—immediately after flushing is performed.

The inventors have discovered that using the relatively small amount of available flushing fluid can be a viable solution to flushing the occlusion. In the broadest respect, the available CSF stored in the device is pressurized to a predetermined amount and then allowed to suddenly, rapidly and forcefully purge the occlusion, in much the same way that a person exhibits while coughing. That is, pressurized CSF can be rapidly released, producing flow jets from the catheter pores into the ventricle. This impulse, or "cough", will push and divert choroid plexus and/or other blockages away from the pores. The device may then be allowed to refill at a slow rate, thus reducing the possibility of rapid suction of fluid back into the system and the attendant possibility of drawing the choroid plexus back into the pores. The catheter at the proximal end may also include back-up pores that can be opened to restart flow from the ventricle should the primary pores remain blocked after a flushing attempt.

According to one aspect, a system for flushing a shunt catheter is disclosed. The system includes a reservoir constructed and arranged to hold a volume of fluid. The reservoir is adapted to communicate with the shunt catheter. An occluder is constructed and arranged to selectively and substantially block drainage from the catheter and from the reservoir. A flow passage from the reservoir to the catheter is also provided. The reservoir is constructed and arranged to allow fluid therein to be pressurized whereby the fluid is rapidly released from the flow passage producing an impulse flow to flush the catheter.

According to another aspect, a flushing device for a shunt catheter is provided. The flushing device includes a reservoir constructed and arranged to hold a volume of fluid. The reservoir is adapted to communicate with the shunt catheter and a drainage path. A valve body defining a conduit allows fluid communication between the reservoir, the shunt catheter and the drainage path. A valve housing is movably disposed within a recess formed in the valve body, in a first position of the valve housing, fluid communication between the reservoir, the shunt catheter and the drainage path is unobstructed and in a second position of the valve housing, fluid communication with the drainage path is blocked. The valve housing includes a check valve having a first position substantially blocking flow from the reservoir to the catheter. The check valve is adapted to open at a predetermined pressure of the pressurized fluid, thereby allowing fluid to be rapidly released producing an impulse flow to flush the catheter.

According to yet another aspect, a catheter is provided. The catheter has a body having a lumen therethrough. A primary set of drain pores is formed in the body and adapted to allow fluid communication with the lumen. A secondary set of drain pores is formed in the body. Each drain pore of the secondary set of drain pores includes a membrane adapted to close the pore. The membrane is constructed and arranged to be ruptured upon application of fluid pressure to open the secondary set of drain pores.

According to still another aspect, a system for flushing a shunt catheter is provided. The system includes a reservoir constructed and arranged to hold a volume of fluid. The reservoir is adapted to communicate with the shunt catheter. A piston-cylinder arrangement communicates with the reservoir. The piston is responsive to pressurized fluid from the reservoir to move to a position substantially blocking drainage from the catheter and from the reservoir. A flow passage from the reservoir to the catheter is provided. The flow passage has a cross-sectional area that is smaller than a cross-sectional area of a lumen of the shunt catheter. The reservoir is constructed and arranged to allow fluid therein to be pressurized whereby the fluid is rapidly released from the flow passage producing an impulse flow to flush the catheter.

It should be appreciated that the foregoing concepts, and additional concepts discussed below, may be arranged in any suitable combination, as the present disclosure is not limited in this respect.

The foregoing and other aspects, advantages, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments will now be described, by way of example, with reference to the accompanying drawings, in which:

FIGS. 7A-7D are schematic perspective views of a portion of the shunt flusher, where

DETAILED DESCRIPTION

Aspects are directed to devices and systems used to flush obstructions in the ventricular catheter. The devices or systems are positioned between the catheter tip and the shunt valve and include a reservoir holding CSF. It should be appreciated that as used herein, "proximal" refers to the upstream portion of the shunt system, such as the catheter side of the shunt system. The proximal side generally extends from the ventricle to the shunt valve. "Distal" refers to the downstream portion of the shunt system, such as the drainage side of the shunt system. The distal side generally extends from the shunt valve to the peritoneum or other CSF resorbtion site. A conduit allows CSF to drain to the shunt valve and to fill the reservoir. In one embodiment, the device also includes a check valve disposed within a valve housing selectively movable between a normal flow position and a backflow position. When in the normal flow position, the check valve and housing allow free flow of CSF through the conduit. When it is desired to back flush the catheter tip, the valve housing and the valve mechanism disposed therein are moved into a position within the conduit where the housing blocks distal flow toward the shunt valve and the valve mechanism within the housing blocks proximal flow toward the catheter unless a predetermined pressure in the reservoir is attained. That is, pressuring the CSF stored in the reservoir causes a sudden opening of the valve mechanism, allowing abrupt proximal flow toward the catheter tip. When the valve mechanism abruptly opens due to this increase in pressure of the CSF from the reservoir, the pressurized CSF can be rapidly released, producing flow jets from the catheter pores into the ventricle. This impulse, or "cough", will push and divert choroid plexus and/or other blockages away from the pores.

In one embodiment, rather than incorporate a separate movable valve housing that blocks distal flow when in the "back flush" position, a flow constricting arrangement that effectively pinches off the distal flow may be provided. In this regard, in one embodiment, a piston-like device is actuated by pressurized CSF blocking distal flow, e.g., pinching the drainage tube.

Another aspect is directed toward the rate at which the reservoir refills. The reservoir is structured to allow CSF to refill at a rate sufficient to prevent or reduce the possibility of drawing the choroid plexus or other obstruction back into the now cleared pores. In one embodiment, the reservoir includes an elastic dome adapted to rebound at slow rate. In one embodiment, the reservoir refills at a rate less than the rate at which fluid flows out of the reservoir when flushing the catheter. In one embodiment, the reservoir refills at a rate between about 2 ml/min and about 10 ml/min. In one embodiment, the reservoir refills at a rate of about 4 ml/min.

In some instances, it is possible that the above-described back flushing procedure will be ineffective at removing the obstruction from the catheter pores. That is, the CSF cannot be pressurized sufficiently to remove the occlusion. Accordingly, to another aspect, the catheter is formed with a secondary set of pores that are normally closed. In one embodiment, these secondary pores cart be ruptured by the pressurized CSF during a back flushing attempt such that flow through the catheter can once again begin. In this regard, while the CSF pressure is insufficient to remove the blockage, the pressure is sufficient to rupture the normally closed secondary pores. In other words, the pressure at which the secondary pores rupture is less than the pressure necessary to flush the lodged obstruction.

Figure 1:
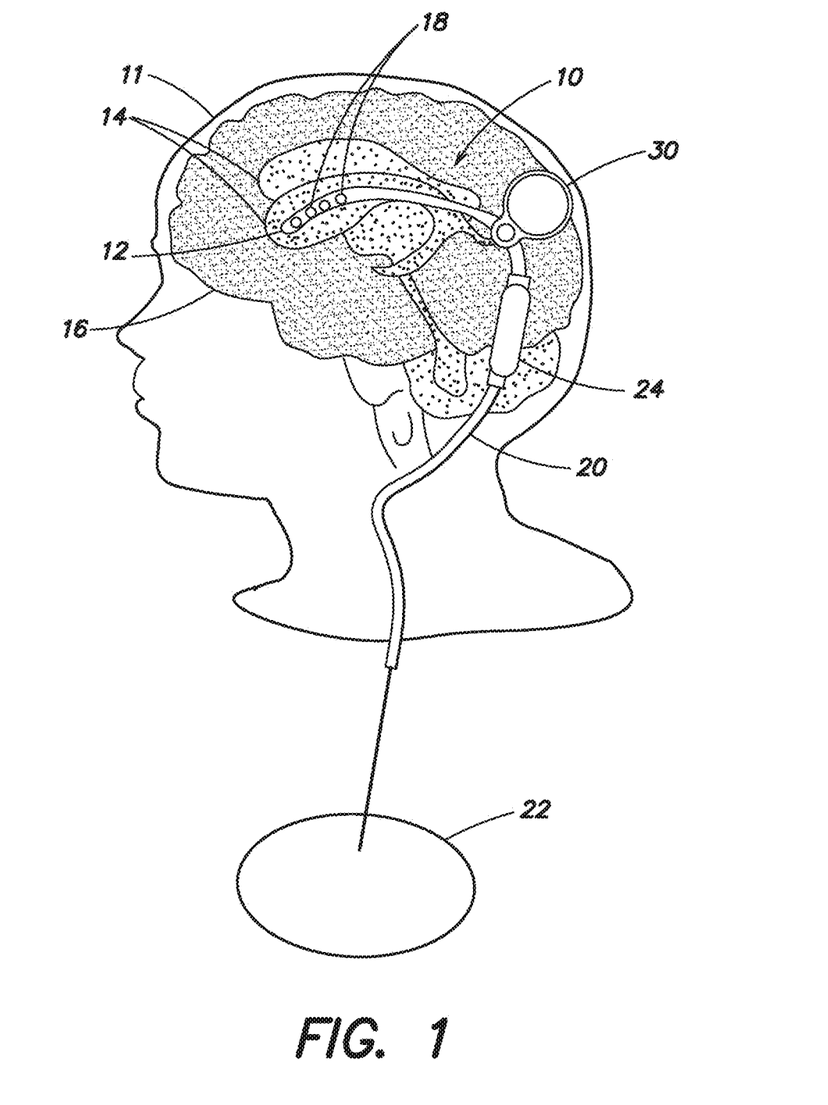
FIG. 1 depicts a schematic representation of a patient fitted with a hydrocephalus shunt system and shunt flusher according to one embodiment.
Figure 2:
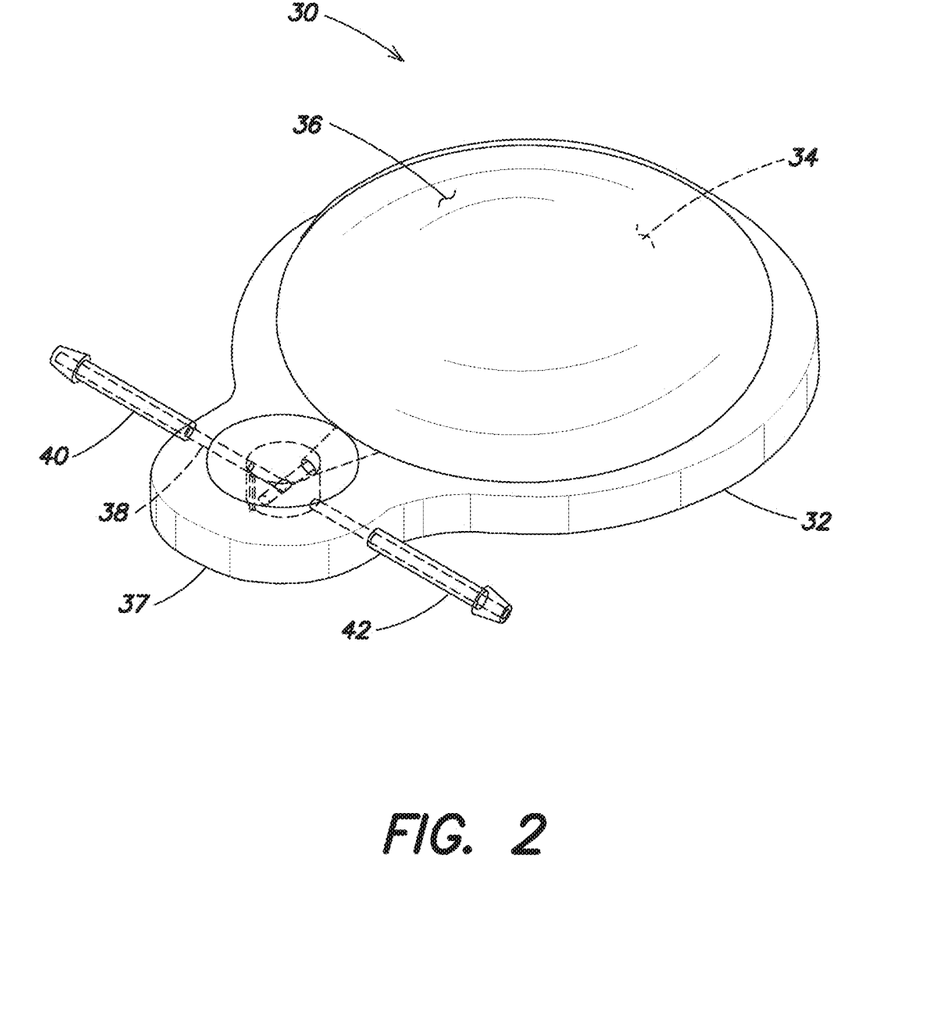
FIG. 2 is a schematic perspective view of one embodiment of the shunt flusher.

Turning now to the figures and in particular FIGS. 1 and 2, one embodiment of the shunt flushing device will now be described. FIG. 1 shows a hydrocephalus shunt arrangement 10 for a patient 11 that including a catheter 12 implanted into at least one lateral ventricle 14 of the patient's brain 16. The proximal end of the catheter 12 includes a plurality of drain holes 18 through which cerebrospinal fluid can enter. The catheter communicates with a drain tube 20 extending distally to the patient's abdominal cavity 22.

As is typical with hydrocephalus shunt arrangements, a shunt valve 24 is disposed between the proximal and distal ends. The shunt valve 24 may be any suitable one-way valve typically found in hydrocephalus shunt systems, the purpose of which is to maintain appropriate levels of CSF pressure within the ventricles yet allow flow out from the ventricle when this pressure is exceeded. In this manner, the check valve cooperates with the tubing system to mimic the natural drainage of the fluid from the ventricles.

Though well understood in the art, one example of a surgical procedure for implanting the shunt is as follows: a hole is formed in the skull and the proximal end of the catheter is inserted through the hole and passed through the brain and into ventricular cavity where the fluid is produced. This tube is then tunneled under the scalp to the one way valve. The valve is placed beneath the skin and is typically situated behind the patient's ear. A distal drain tube is coupled to the one way valve and tunneled subcutaneously to the peritoneal cavity of the abdomen where the fluid drains and is absorbed by the lining, then absorbed by the veins of the lining and transported to the kidneys for excretion. Neurosurgeons have been performing this procedure to treat hydrocephalus for many years.

According to one aspect, the hydrocephalus shunt arrangement 10 also includes a flushing device 30 located between the ventricular catheter 12 and the shunt valve 24. Like the one way valve, the flushing device is also implanted beneath the skin at a location near the patient's ear. The device is suitable as a preventive retrograde flushing mechanism and is depicted in more detail in FIG. 2. As mentioned, the flushing device 30 integrates into a conventional system between the catheter 12 and shunt valve 24. In one embodiment, the flushing device 30 includes a base 32 and a dome-shaped reservoir 34 defined between a pliable membrane 36 and the base 32. The pliable membrane may be made from silicone elastomer or Silastic brand silicone elastomer available from Dow Chemical, the thickness of which may be sized to result in the above-mentioned reservoir refill rates. Without wishing to be bound by theory, the refill rate will be greatest when the reservoir chamber is empty and the refill rate will decrease as the reservoir refills and the refill rate will be proportional to the intracranial pressure, and inversely proportional to the elasticity of the chamber wall and to the overall tubing impedance. Also, the design of the shape of the dome may have nonlinear properties so as to initiate the refill more slowly, with thinner walls in the part of the dome which would naturally start to refill first, for example. Further, the curvature of the wall could be non-uniform. The dome-shaped reservoir accumulates enough cerebrospinal fluid for efficient flushing. In one embodiment, the reservoir volume is between about 0.5 ml and about 3 ml. In one embodiment, the reservoir volume is about 2 ml.

The base 32, in the embodiment shown, includes a protruding ear 37 having a conduit 38 therein. The conduit 38 is coupled to a proximal port 40 and a distal port 42, with the proximal port connectable to the catheter 12 and the distal port connectable to the shunt valve 24. As shown, the ports include couplings that can attach to the catheter tube and the tube leading to the shunt valve. However, as can be appreciated, the catheter tube and the tube leading to the shunt valve can be integrally formed with the flushing device. Of course, it should be appreciated that other suitable arrangements for the flushing device are contemplated. For example, no base member is required and instead the reservoir can formed as a balloon-like member coupled to the conduit 38.

Figure 3A:
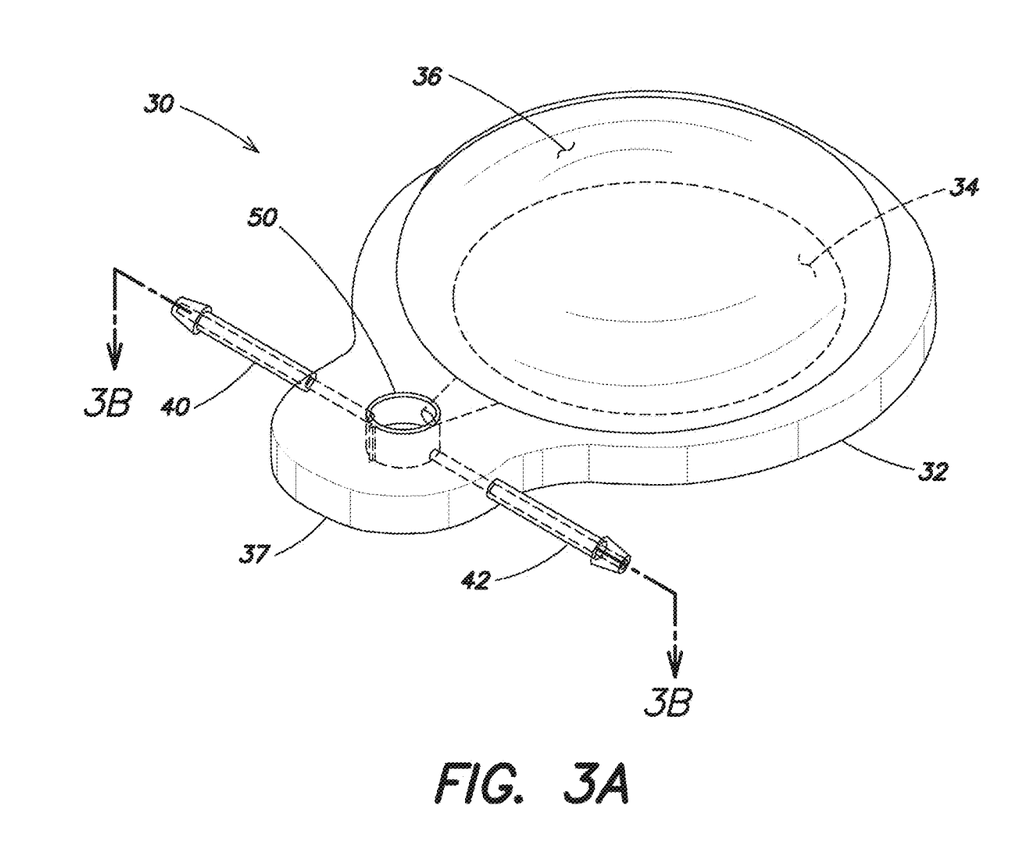
FIG. 3A a schematic perspective view of one embodiment of the shunt flusher and FIG. 3B is a partial cross-sectional view taken along line 3B-3B of FIG. 3A.
Figure 3B:
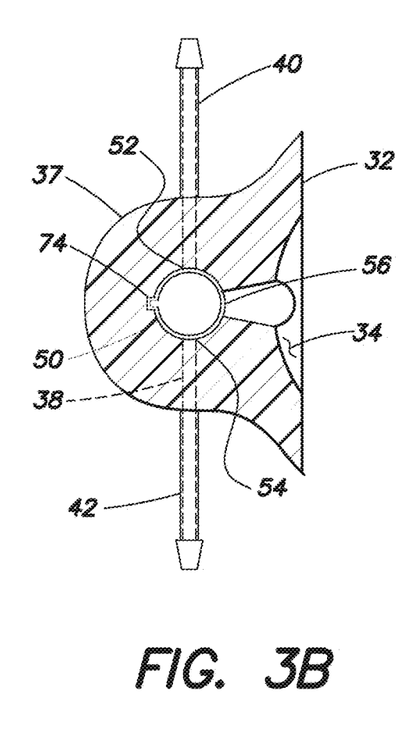

In one embodiment, as shown in FIGS. 3A and 3B, the conduit of the flushing device 30 includes a recess area 50 that receives a valve housing as will be explained in more detail below. The recess area 50 also includes an inlet port 52 in fluid communication with the proximal port 40, an outlet port 54 in fluid communication with the distal port 42 and a reservoir port 56 in fluid communication with the reservoir 34. It should be appreciated that the ear 37 having the conduit 38 with recess area 50 need not be integrally formed with the base 32. Instead, the ear 37 may be separate from the reservoir but attached to the reservoir using a suitable coupling. In this regard, the ear 37 can be considered a valve body including the conduit and receiving the valve housing.

Figure 4A:
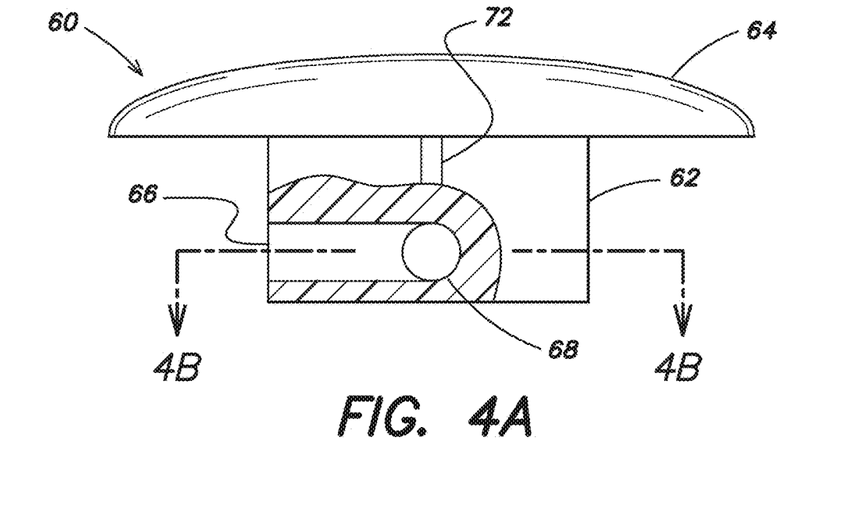
FIG. 4A is a schematic side view of a portion of the shunt flusher and FIG. 4B is a cross-sectional view taken along line 4B-4B of FIG. 4A.
Figure 4B:
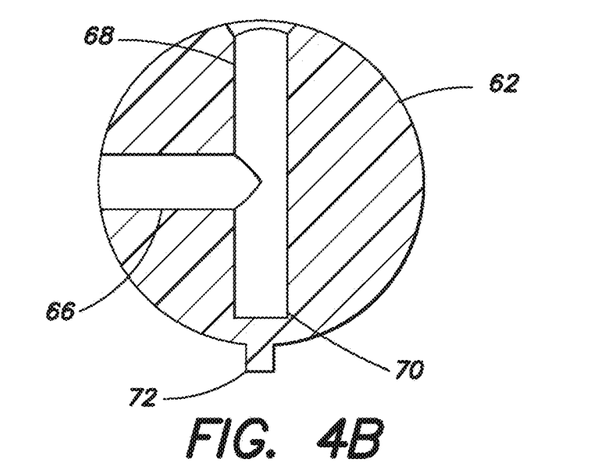

FIGS. 4A and 4B show an embodiment of the valve housing 60. The valve housing includes a body 62 and a cap 64. The body 62 is sized to fit within the recess area 50. The body 62 includes catheter port 66 and a reservoir port 68. Opposite the reservoir port is a check valve chamber 70, the structure and function of which will be described in detail below. The valve housing is biased such that the, body is disposed away from the conduit (i.e., tending to push the body out of the recess) such that the flow in the conduit 38 (i.e., between the inlet port 52, outlet port 54 and reservoir port 56) is unobstructed. The valve housing can be retained in the recess via any suitable capturing arrangement. Further, the valve body 62 housing includes a key 72 that slides in a keyway 74 formed in the recess (see FIG. 3B) so that the ports remain properly aligned. When the valve housing is pushed or otherwise moved into the recess area, the outlet port 54 becomes blocked by the valve body 62 and fluid communication can only occur between the reservoir port 56 and the inlet port 52. As can be seen, the valve housing body 62 does not include any port that can communicate with the outlet port 54 such that when the valve housing is depressed into the recess area 50, any flow to the outlet port 54 and subsequently through the distal port 42 and out to the abdominal cavity is effectively restricted by the valve body 62. Thus, the valve body 62 acts as an occluder to substantially block drainage from the catheter (e.g., to the drain tube) and from the reservoir (e.g., to the drain tube).

Figure 5:
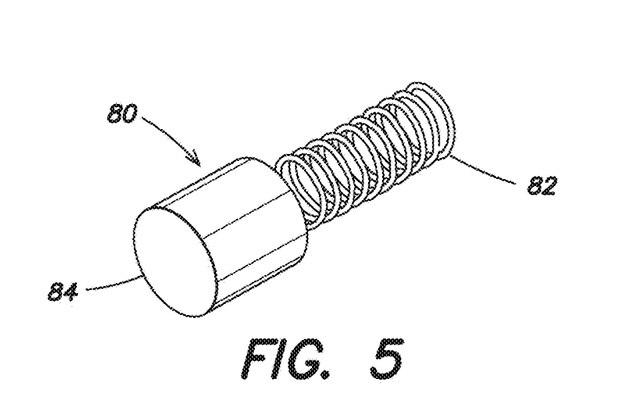
FIG. 5 is a schematic perspective view of one embodiment of a valve mechanism of the shunt flusher.

The valve chamber 70 is configured to receive a valve mechanism 80. The valve mechanism, in one embodiment, is formed as a spring 82 and piston 84 arrangement, as shown in FIG. 5. It should be appreciated that although the valve mechanism is shown as a coil spring and cylindrical piston, other suitable arrangements may be employed. For example, a ball may be used in place of the piston 84, as is the case in a conventional check valve. Similarly, other suitable springs may be used, such as a leaf spring, Belleville spring, torsions spring, etc.

Figure 6A:
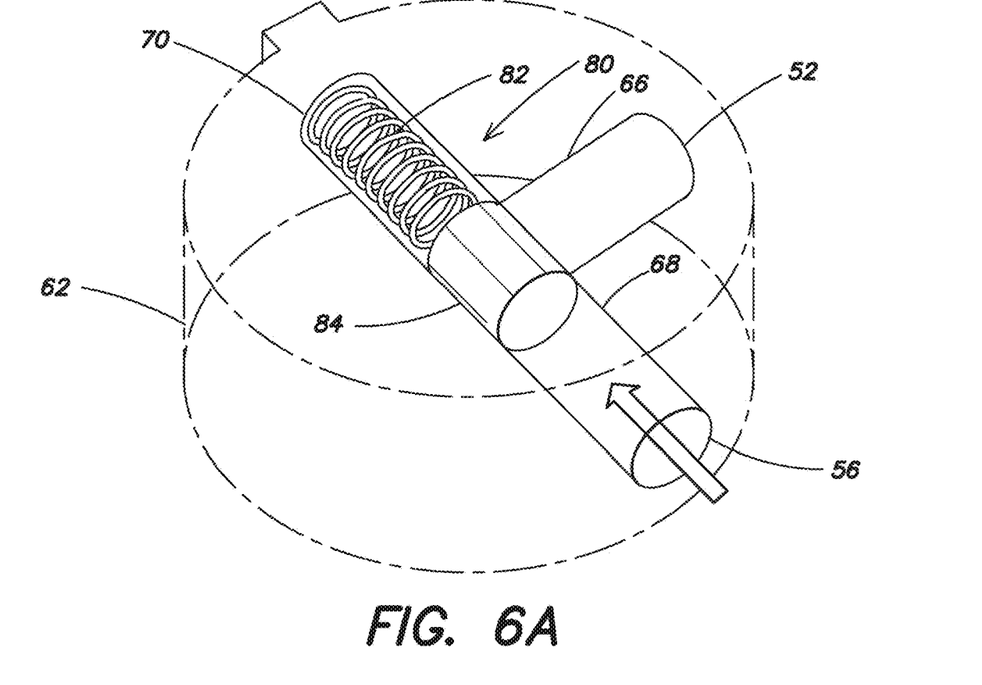
FIGS. 6A and 6B are schematic perspective views of a portion of the shunt flusher.
Figure 6B:
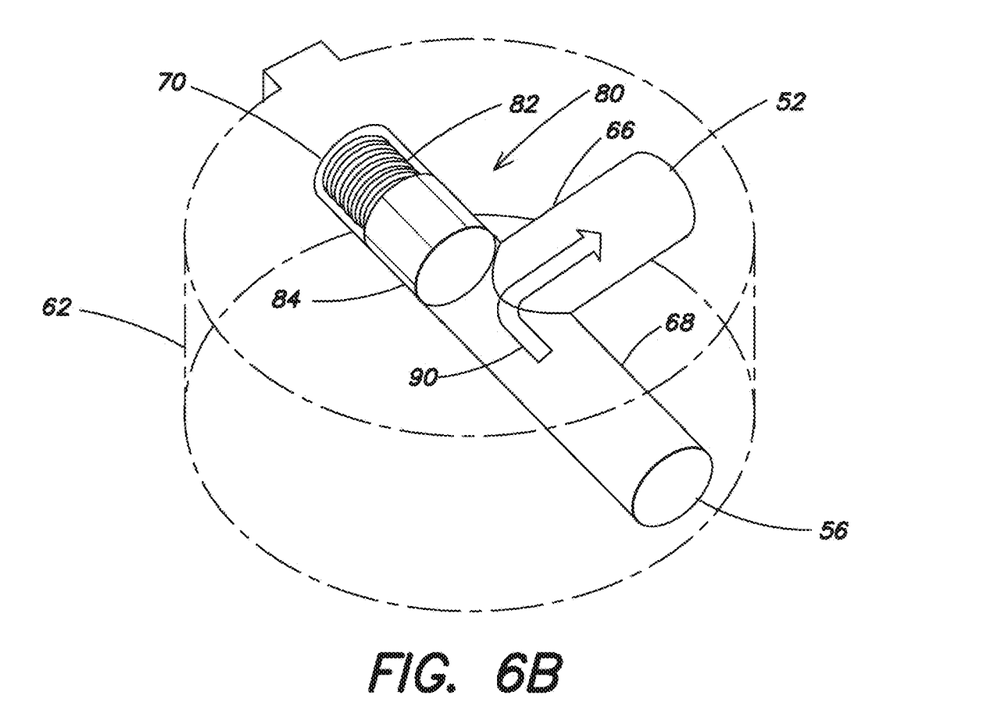

In the normal mode of operation, the valve mechanism 80 is positioned such that the valve piston 84 blocks flow from the reservoir port 56 to the inlet port 52. When the pressure in the reservoir increases, as for example, upon depression of the dome-shaped membrane 36, the spring force is overcome and fluid flow out of the reservoir 34 through the reservoir port 56 and out through the inlet 52 is allowed to commence. This sequence is represented schematically in FIGS. 6A and 6B. In FIG. 6A, the valve mechanism is shown in its normally blocked position. In FIG. 6B, as pressure increase above a threshold (as set by the spring rate of the spring 82), the piston allows a sudden fluid release along arrow 90 from the reservoir port 56 to the inlet port 52.

In one embodiment, the force at which the valve mechanism opens may be fixed for a given spring used in the valve mechanism or may be adjusted by the surgeon. Suitable arrangements for adjusting the spring force will be apparent to those of skill.

Of course, it is to be appreciated that under normal operating conditions, when flushing of the catheter is not required, the valve housing and as a result the valve mechanism are not within the fluid conduit between the proximal inlet port, the distal outlet port and the reservoir, such that open fluid communication between these three ports is possible. However, when flushing is required, the valve mechanism, through the movement of the valve housing into the recess, blocks the flow of flushing fluid out from the reservoir and into the proximal inlet port until the force of the spring is exceeded. This produces the "cough-like" or impulse force to open the blockage. Utilizing this "cough-like" or impulse force of fluid allows for a relatively small amount of fluid flow to open the blockage in the catheter.

Figure 12:
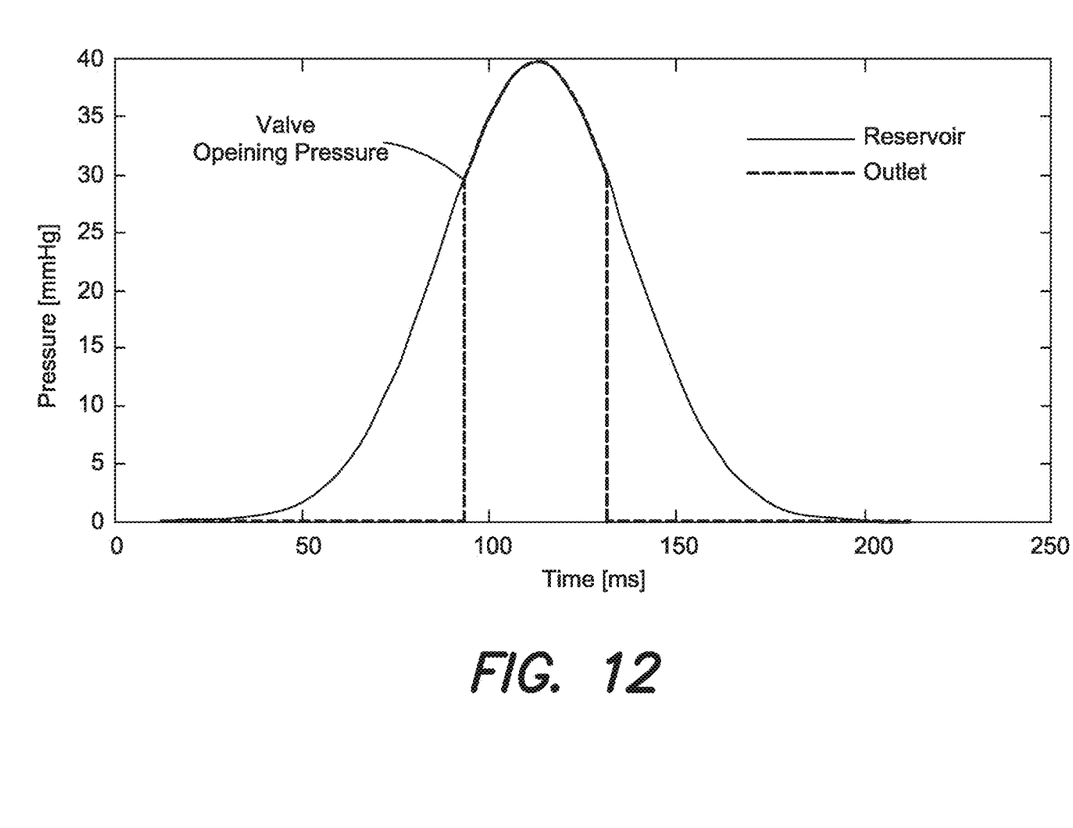
FIG. 12 is a graph showing fluid pressure (relative to intracranial pressure) vs. time.

Thus, the flushing device acts as a retrograde flushing device, which opens a ventricular catheter tip obstruction by rapidly "coughing out" liquid available in the reservoir. Most of the time, the device serves as a passive element of the shunting system and has no effect on the normal functioning of the shunting system. However, when flushing is desired the operator (typically a physician) pushes down the valve housing through the patient's skin, thus making the valve mechanism "operational". The operator/physician applies pressure on the CSF-filled dome. As pressure builds, the valve mechanism holds back the flow until the pressure exceeds the valve spring opening parameters whereupon pressurized CSF rushes out and through the catheter tip, cleaning its pores and pushing away choroid plexus. As seen in FIG. 12, the pressure inside the reservoir builds, yet the valve mechanism holds back the flow until the pressure exceeds the opening parameters of the valve, allowing the impulse of pressurized fluid to rush out and clear the obstruction.

Figure 7A:
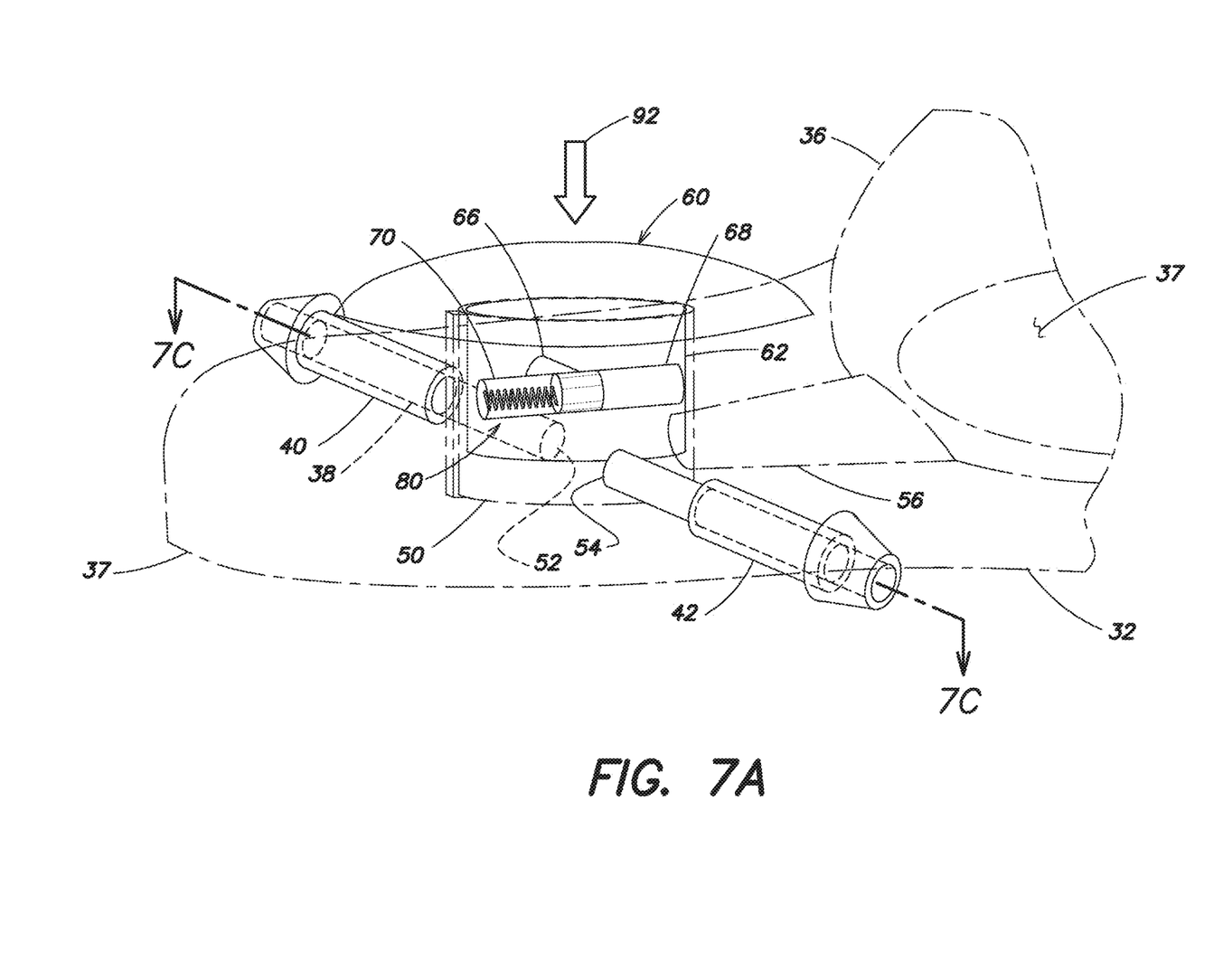
Figure 7B:
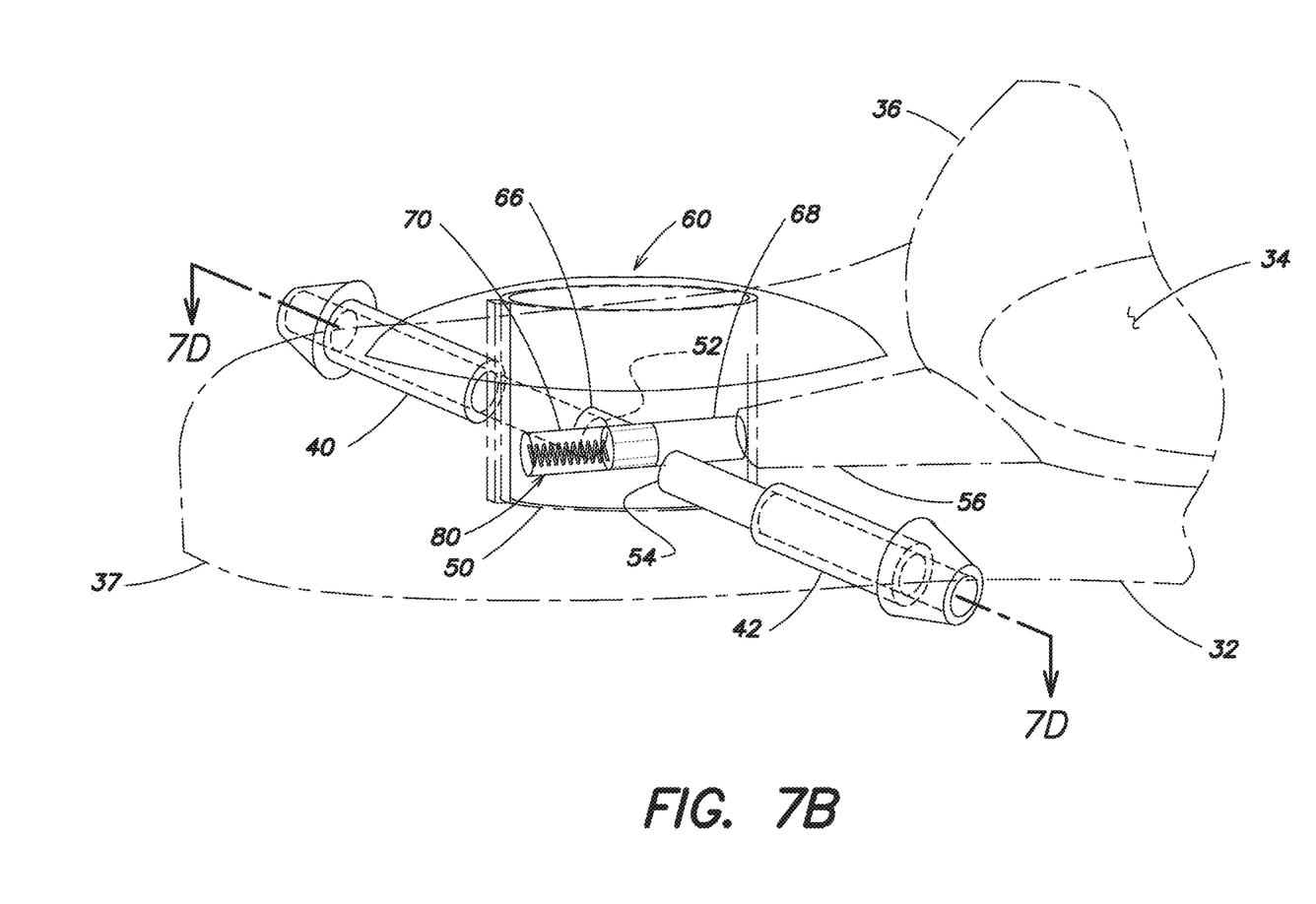
Figure 7C:
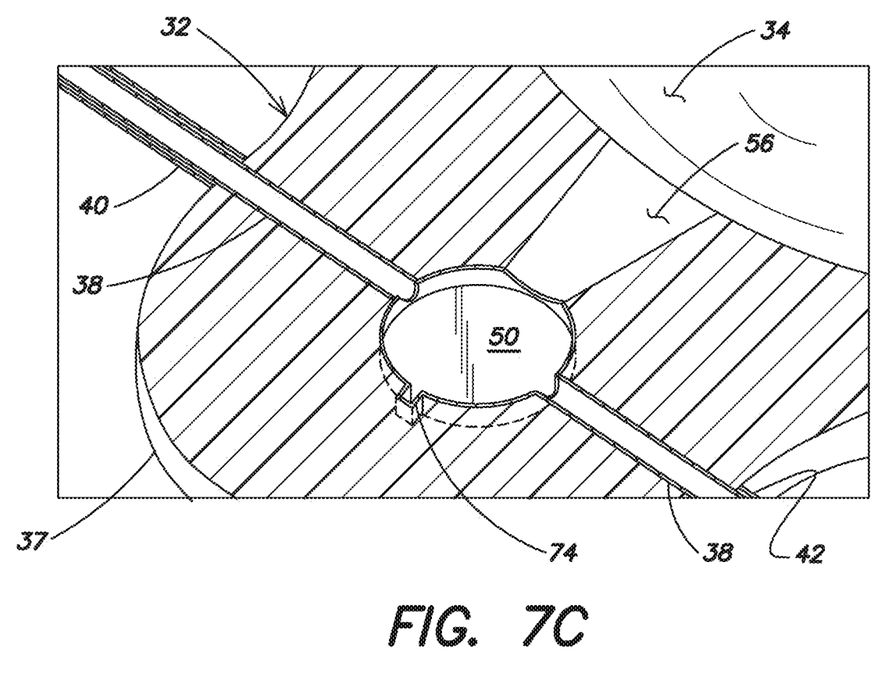
FIG. 7C is a partial cross-sectional view taken along line 7C-7C of FIG. 7A
Figure 7D:
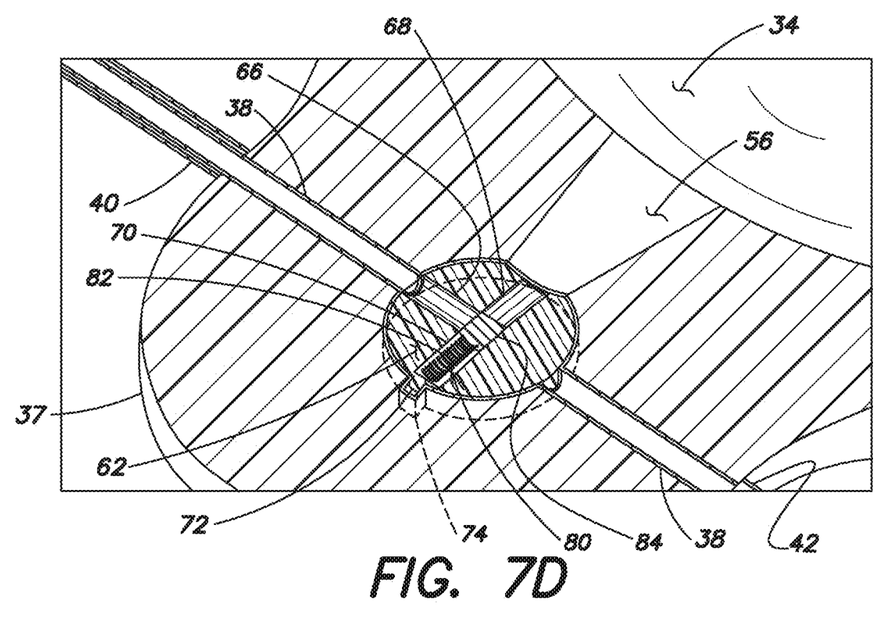
FIG. 7D is a partial cross-sectional view taken along line 7D-7D of FIG. 7B.

As discussed above, in one embodiment, the valve housing 60 has two modes of operation, as best shown in FIGS. 7A-7D. The normal state of the valve housing is the upper or retracted position, as shown in FIGS. 7A and 7C. When flushing is required, the valve housing and associated valve mechanism is engaged by pushing on the cap 64 such that the valve housing 60 moves downwards along arrow 92 (FIG. 7A) and the valve housing body 62 into the recess area 50, as shown in FIGS. 7B and 7D. In the first mode, the valve housing 60 and associated valve mechanism 80 is in the upward position and the proximal and distal ports and the reservoir chamber are in fluid communication to allow a normal operation of the shunting system (FIGS. 7A and 7C). In the second mode (i.e., flushing mode), the cap 64 of the valve housing 60 is pushed down, with the valve body 62 occluding the distal port and the spring 82 forces the piston 84 to block flow to the proximal port 42. Pressure can be exerted on the reservoir chamber dome 36, and once the pressure exceeds the spring force of spring 82, liquid rushes suddenly from the reservoir chamber 34 towards the catheter through the conduit 38, and in particular through ports 68 and 66. This flow can be best described as a rapid flushing that occurs as pressure rises above some predetermined threshold value sufficient to drive the piston away from its seat, allowing flow into the proximal port and towards the catheter. After flushing is completed, the valve housing is released again, allowing it to move to its normal position, restoring normal flow communication in the shunt system. The valve housing may automatically move to its normal (i.e., unobstructing) position by the action of a spring bias. Other suitable arrangements for resetting the valve housing may be employed. Finally, the chamber is released as well and it slowly regains its shape and fills up with fluid. In this regard, the dome of the reservoir is constructed to return to its pre-depressed position at a relatively slow rate to limit the possibility of drawing in the occlusion (e.g., the choroid plexus) back into the pores. Once the reservoir refills, the process can be repeated. It should be appreciated that the system may be activated, that is, the flushing procedure may commence when the patient is either standing, sitting, or lying down and can be activated by any operator such as the patient himself or herself, a physician or a care taker.

Figure 8:
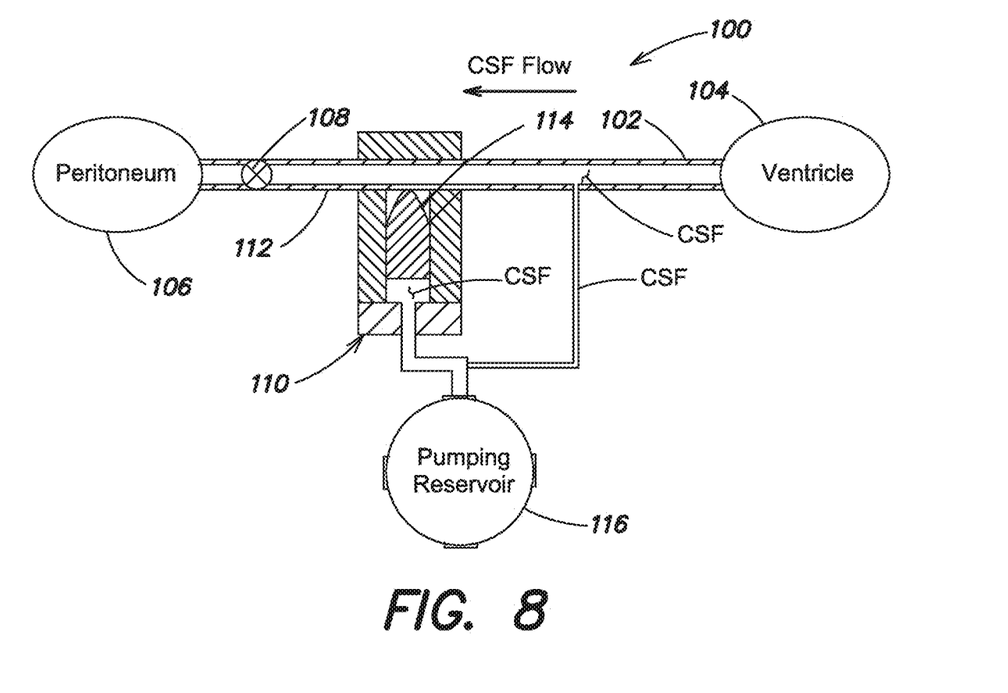
FIGS. 8 and 9 are schematic representations of another embodiment of a shunt flushing arrangement.
Figure 9:
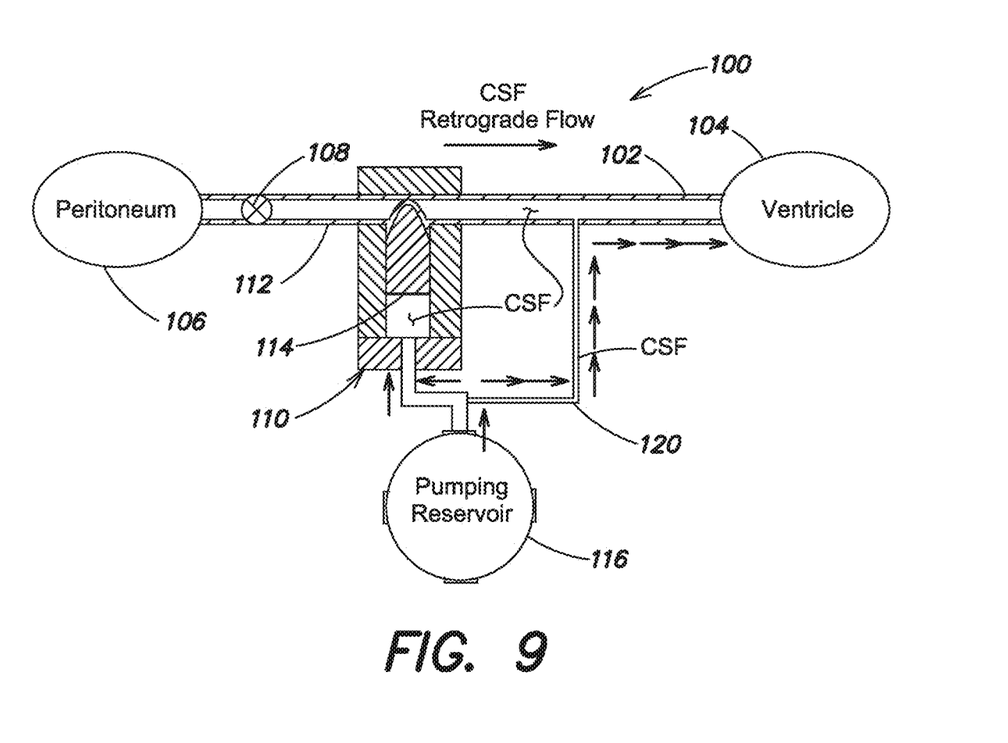

In another embodiment, rather than employ a separate valve housing and valve mechanism that is separately moved into a position that blocks outflow through the distal port, the flushing system may incorporate an automatic mode, whereupon pressure exerted on the reservoir dome first causes the distal port to become blocked. Increased pressure in the reservoir then causes fluid to flow toward the catheter to unblock the occlusion. A schematic representation of such an embodiment is shown in FIGS. 8 and 9. As shown in FIG. 8, the shunt system 100 includes a catheter tube 102 allowing CSF flow out of the ventricle 104 and into the abdominal cavity or peritoneum 106 through shunt valve 108. In this embodiment, a pressure-actuated occluder 110 acts on the distal side 112 (whether the distal port, the distal tube communicating with the shunt valve, or any other location blocking flow toward the abdominal cavity). The occluder includes a piston-cylinder device 114 that is subjected to pressurized CSF such that the piston can move in the cylinder in response to fluid pressure from the reservoir 116. The cylinder of the piston-cylinder arrangement in one embodiment surrounds the drain tube.

As shown in FIG. 9, the piston 114 of the occluder 110 then moves into a position blocking the flow. The piston 114 can act to pinch the distal tube or other outflow tube or port. Once the outflow is blocked, retrograde fluid flow to the ventricular catheter can commence to clear any blockage. Fluid from the reservoir 116 flows to the ventricular catheter 102 through a relatively smaller diameter tube 120 (e.g., smaller than the cross-sectional area of the catheter lumen). No additional valve mechanism is present in this embodiment, as the smaller diameter tube 120 (or at least a portion thereof) in the normal mode of the shunt operation is closed. As the pressure builds upon application of a pumping force on the reservoir, the normally closed smaller diameter tube pops open to produce the impulse force allow the flushing fluid to clear the blockage from the catheter pores. This is also depicted, for example, in FIG. 12 (though a valve per se may not be used in some embodiments, as discussed above). Of course, a valve mechanism, such as the spring-piston arrangement described above or a pliable duck-bill valve arrangement may also be used in this embodiment (either in combination with the smaller diameter retrograde tube or in combination with a larger diameter retrograde tube).

In this embodiment, though not shown, a separate reservoir refill line may be included such that after a flushing process is complete, the reservoir can refill with CSF. As discussed above, the reservoir refills at a relatively slow rate via this refill line.

Figure 10:
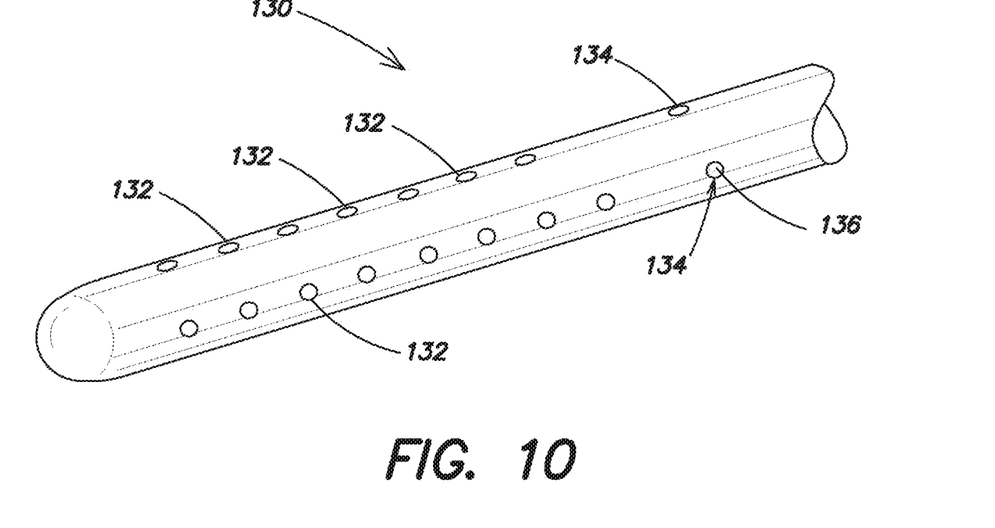
FIGS. 10 and 11 are schematic perspective views of a portion of one embodiment of a catheter.
Figure 11:
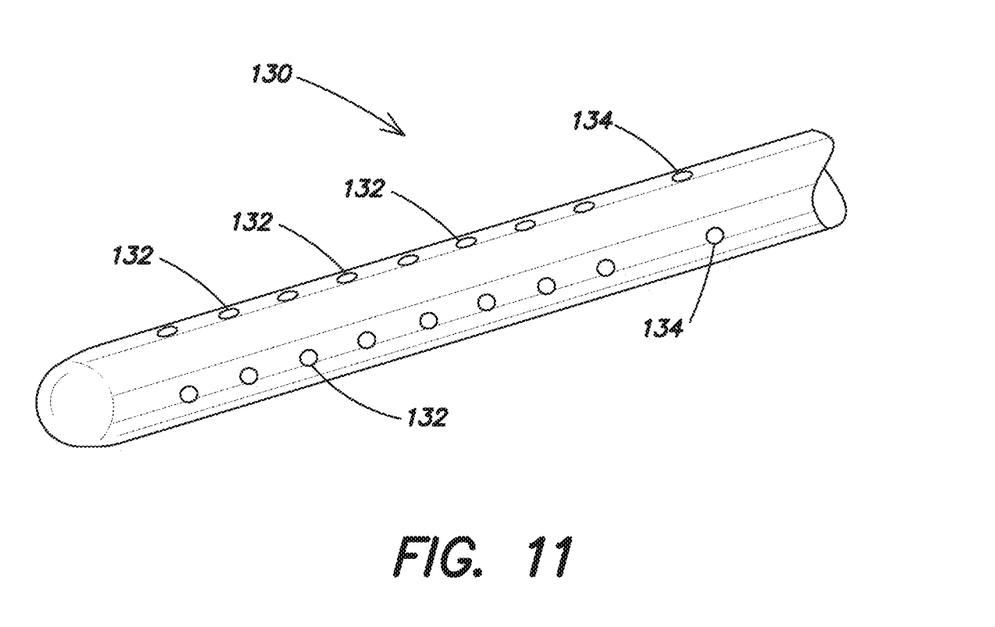

In one embodiment, as shown in FIG. 10, the catheter tube 130 includes a tube body having a lumen therethrough, a primary set of drainage pores 132 or openings communicating with the lumen and a secondary, normally closed set of drainage pores 134. In this way, should the primary set of pores become, permanently blocked, that is, the flushing device is unable to unblock the primary set of pores, then the second set of pores may be opened, allowing fluid flow out of the catheter once again.

The secondary pores may be opened using any suitable method or arrangement. For example, the pores may be covered with a material that will rupture under MRI or ultrasonic energy.

In one embodiment, each secondary pore 134 is formed with a thin membrane 136 covering the pore opening, as shown in FIG. 10. Upon pressurizing the flushing fluid, in any of the ways described above or other ways, while the pressure is unable to flush the blockage at the primary pores, the pressure is sufficient to rupture the membrane covering the secondary pores. Such rupturing opens the secondary pores 134 to allow fluid flow from the ventricles.

In another embodiment, not shown, the secondary pores may be formed of a deformable metal having a duck-bill slit. Upon application of fluid pressure, the fluid forces the metal bills to splay open. Because the metal will have been deformed beyond its elastic limit, the pores will remain open to receive CSF fluid into the catheter.

In one embodiment, the membrane ruptures or the duck-bill slit opens at a pressure of about 10 torr greater than the anticipated pressure necessary to unblock the pores. Thus, in one embodiment, the anticipated pressure necessary to unblock the pores is about 40 torr and thus the membrane ruptures (or the buck-bill slit opens) at a pressure of about 50 torr.

Several different techniques or arrangements for providing the pressurized fluid to open the secondary pores may be employed. In one embodiment, the fluid in the reservoir may be pressurized to the higher degree to open the secondary pores by changing a valve setting on the pumping reservoir (for example, with magnets or other suitable techniques). In another embodiment, pumping the fluid from two different reservoirs may be employed. For example, one of the pumping reservoirs (and associated valve arrangement if employed) would allow the fluid to be pressurized only as high as contemplated to open the occluded catheter pores, so that the effect on the shunt would be to expel choroid plexus and other tissues or occlusions, but not to open the secondary pores. If this fails to improve shunt function by clearing the occlusion from the primary pores, the other reservoir may be pumped. This secondary reservoir (and associated valve arrangement if employed) would provide a pressure above the threshold to open the secondary pores. In each embodiment, the operator (typically the physician though it could be the patient) would know that the reservoir and/or valve arrangement of the first embodiment or the primary reservoir of the second embodiment failed to clear the occlusion (as the patient would remain symptomatic) and that the secondary pores have not yet been opened. Then the physician typically would reset the valve in the case of the first embodiment or act on the secondary reservoir in the case of the second embodiment to open the secondary pores.

The various components described are formed of typical biocompatible materials typically used in shunt systems to treat hydrocephalus. One example of such a material is silicone elastomer or Silastic brand silicone elastomer available from Dow Chemical. Similarly, the catheter and other drain tubes as well as the shunt valve are sized to typical dimensions and have typical characteristics associated with conventional shunt systems. In one embodiment, a conventional, "off-the-shelf" hydrocephalus shunt system is employed, and is modified between the catheter and shunt valve to accept the above described flushing device/system. That is, the tube leading from the catheter to the shunt valve is inserted with the flushing device/system.

Having thus described several aspects of at least one embodiment of this invention, it is to be appreciated various alterations, modifications, and improvements will readily occur to those skilled in the art. For example, the device/system described herein may be adapted for surgical placement in other locations and/or to treat other conditions beyond hydrocephalus. Such alterations, modification, and improvements are intended to be part of this disclosure, and are intended to be within the spirit and scope of the invention. Accordingly, the foregoing description and drawings are by way of example only.

What is claimed is:

1. A system for flushing a shunt catheter, the system comprising:
   a catheter comprising:
      a body having a lumen therethrough;
      a primary set of drain pores formed in the body and configured to allow fluid communication with the lumen;
      a secondary set of drain pores formed in the body, with each drain pore of the secondary set of drain pores comprising a membrane configured to close the pore, the membrane being constructed and arranged to be ruptured upon application of fluid pressure to open the secondary set of drain pores; and
   a pressure source configured to apply the fluid pressure to the lumen of the body to rupture the membrane.

2. The system of claim 1, wherein the membrane is configured to cover an opening of each drain pore of the secondary set of drain pores.

3. The system of claim 1, wherein, during normal operation of the catheter, the secondary set of drain pores is closed.

4. The system of claim 1, wherein the body includes a tubular body.

5. The system of claim 1, wherein, upon rupturing of the membrane, fluid flows out of the catheter.

6. The system of claim 1, wherein the membrane is configured to be ruptured at a pressure less than a pressure to unblock the primary set of drain pores.

7. The system of claim 1, wherein each drain pore of the primary set of drain pores includes an opening in the body.

8. The system of claim 1, wherein the pressure source includes a reservoir constructed and arranged to hold a volume of fluid, the reservoir configured to communicate with the catheter.

9. The combination of claim 8, wherein the fluid in the reservoir is configured to apply the fluid pressure to rupture the membrane.

10. The system of claim 9, wherein the reservoir comprises a pumping reservoir configured to pressurize the fluid to a first pressure to rupture the membrane.

11. The system of claim 1, wherein the membrane is constructed and arranged to be ruptured upon application of the fluid pressure to open the secondary set of drain pores when the application of the fluid pressure fails to unblock the primary set of drain pores.

12. A ssytem for flushing a shunt catheter, the system comprising:
   a catheter, comprising:
      a body having a lumen therethrough;
      a primary set of drain pores formed in the body and configured to allow fluid communication with the lumen;

a secondary set of drain pores formed in the body, with each drain pore of the secondary set of drain pores comprising a membrane configured to close the pore, the membrane being constructed and arranged to be ruptured upon application of fluid pressure to open the secondary set of drain pores, and a pumping reservoir in fluid communication with the catheter, the pumping reservoir configured to hold a volume of fluid and configured to pressurize the fluid to rupture the membrane.

13. The system of claim 12, wherein the pumping reservoir is a first pumping reservoir configured to pressurize the fluid to a first pressure to rupture the membrane, and further comprising a second pumping reservoir configured to pressurize the fluid to a second pressure anticipated to be sufficient to unblock the primary set of drain pores, the second pressure lower than the first pressure.

14. The system of claim 13, wherein the first pressure is selected to be about 10 torr greater than the second pressure.

* * * * *

UNITED STATES PATENT AND TRADEMARK OFFICE
CERTIFICATE OF CORRECTION

| | |
|---|---|
| PATENT NO. | : 11,896,789 B2 |
| APPLICATION NO. | : 16/654921 |
| DATED | : February 13, 2024 |
| INVENTOR(S) | : Joseph Madsen et al. |

It is certified that error appears in the above-identified patent and that said Letters Patent is hereby corrected as shown below:

In the Claims

In Claim 9, at Column 10, Lines 50-51:
"9. The combination of claim 8, wherein the fluid in the reservoir"

Should read:
--9. The system of claim 8, wherein the reservoir--

In Claim 12, at Column 10, Line 61:
"12. A ssytem for flushing a shunt catheter, the system"

Should read:
--12. A system for flushing a shunt catheter, the system--

Signed and Sealed this
Sixteenth Day of April, 2024

Katherine Kelly Vidal
*Director of the United States Patent and Trademark Office*